United States Patent [19]

Raddatz et al.

[11] Patent Number: 4,746,649

[45] Date of Patent: * May 24, 1988

[54] DIAMINO ACID DERIVATIVES

[75] Inventors: Peter Raddatz, Darmstadt; Claus Schmitges, Gross-Umstadt, both of Fed. Rep. of Germany

[73] Assignee: Merck Patent Gesellschaft mit beschraenkter Haftung, Darmstadt, Fed. Rep. of Germany

[*] Notice: The portion of the term of this patent subsequent to May 19, 2004 has been disclaimed.

[21] Appl. No.: 33,366

[22] Filed: Apr. 2, 1987

Related U.S. Application Data

[62] Division of Ser. No. 735,247, May, 1985, Pat. No. 4,666,888.

[30] Foreign Application Priority Data

May 18, 1984 [DE] Fed. Rep. of Germany ....... 3418491

[51] Int. Cl.$^4$ ...................... A61K 37/02; C07K 5/02; C07K 5/10
[52] U.S. Cl. ........................................ 514/18; 514/19; 530/330; 530/331; 530/332
[58] Field of Search ................... 514/18, 19; 530/330, 530/331, 332

[56] References Cited

U.S. PATENT DOCUMENTS 4,666,888 5/1987 Raddatz et al. ..................... 514/18

Primary Examiner—Delbert R. Phillips
Attorney, Agent, or Firm—Millen & White

[57] ABSTRACT

New diamino acid derivatives of the formula I $$X-Z-NH-CH(CH_2R^1)-CH(NH_2)-CH_2-CO-E-G-Y \quad I$$

wherein

X is H, $R^2-O-C_nH_{2n}-CO-$, $R^2-C_nH_{2n}-O-CO-$, $R^2-C_nH_{2n}-CO-$, $R^2-SO_2$, $(R^2-C_nH_{2n})-L(R^2-C_rH_{2r})-C_tH_{2t}-CO-$, $H-(NHCH_2CH_2)_n-NH-CH_2CO-$ or 9-fluorenyl$-C_nH_{2n}-O-CO-$, Z is 0 to 4 amino acid radicals, bonded to one another in a peptide-like manner, selected from the group consisting of Abu, Ada, Ala, Arg, Dab, Gly, His, Ile, Leu, tert.-Leu, Lys, Met, Nbg, Nle, N-Me-His, N-Me-Phe, Orn, Phe, Pro, Ser, Thr, Tic, Trp, Tyr and Val, $R^1$ is H, A, cycloalkyl with 3-7 C atoms, Ar or $C_pH_{2p}-W$, E is absent or is Ala, Gly, Ile, Leu, tert.-Leu, Met, Ser, Thr or Val, G is absent or is His, Phe, Trp, Tyr or $-NH-CH(CH_2R^1)-CH(NH_2)-CH_2CO-$, Y is $-O-C_mH_{2m}-R^3$, $-NH-C_mH_{2m}-R^3$, $-NH-C_mH_{2m-1}(R^3)_2$ or $NA_2$, $R^2$ is A, cycloalkyl with 3-7 C atoms, benzyl or Ar, L is CH or N, $R^3$ is H, A, cycloalkyl with 3-7 C atoms, Ar, pyridyl, imidazolyl, piperidyl, N-benzyl-piperidyl or piperazinyl, W is OH, $NH_2$, OA, NHA or $NA_2$, A is alkyl with 1-6 C atoms, Ar is unsubstituted phenyl, phenyl which is mono- or polysubstituted by A, AO, F, Cl, Br, I, $CF_3$ and/or $NH_2$, or unsubstituted naphthyl and m, n, p, r and t are each 0, 1, 2, 3, 4 or 5, and salts thereof, inhibit the activity of human plasma renin.

10 Claims, No Drawings

DIAMINO ACID DERIVATIVES

This is a division, of application Ser. No. 735,247 filed May 17, 1985 now U.S. Pat. No. 4,666,888.

BACKGROUND OF THE INVENTION

This invention relates to new diamino acid compounds having valuable properties.

Similar compounds are known from European Patent Application No. 77,028.

SUMMARY OF THE INVENTION

It is an object of the invention to provide new compounds with usefull properties, in particular those which can be used for the preparation of medicaments.

Upon further study of the specification and appended claims, further objects and advantages of this invention will become apparent to those skilled in the art.

These objects have been achieved by providing new diamino acid derivatives of the formula I

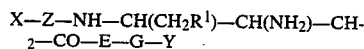

$$X-Z-NH-CH(CH_2R^1)-CH(NH_2)-CH_2-CO-E-G-Y \qquad I$$

wherein

X is H, $R^2-O-C_nH_{2n}-CO-$, $R^2C_nH_{2n}-O-CO-$, $R^2-C_nH_{2n}-CO-$, $R^2-SO_2$, $(R^2-C_nH_{2n})-L(R^2-C_rH_{2r})-C_tH_{2t}-CO-$, $H-(NHCH_2CH_2)_n-NH-CH_2CO-$ or 9-fluorenyl-$C_nH_{2n}-O-CO-$, Z is 0 to 4 amino acid radicals, bonded to one another in a peptide-like manner, selected from the group consisting of Abu, Ada, Ala, Arg, Dab, Gly, His, Ile, Leu, tert.-Leu, Lys, Met, Nbg, Nle, N-Me-His, N-Me-Phe, Orn, Phe, Pro, Ser, Thr, Tio, Trp, Tyr and Val, $R^1$ is H, A, cycloalkyl with 3-7 C atoms, Ar or $C_pH_{2p}-W$.

E is absent or is Ala, Gly, Ile, Leu, tert.-Leu, Met, Ser, Thr or Val,

G is absent or is His, Phe, Irp, Tyr or $-NH-CH(CH_2R^1)CH(NH_2)-CH_2CO-$,

Y is $-O-C_mH_{2m}-R^3$, $-NH-C_mH_{2m}-R^3$, $-NH-C_mH_{2m-1}(R^3)_2$ or $NA_2$, $R^2$ is A, cycloalkyl with 3-7 C atoms, benzyl or Ar, L is CH or N, $R^3$ is H, A, cycloalkyl with 3-7 C atoms, Ar, pyridyl, imidazolyl, piperidyl, N-benzyl-piperidyl or piperazinyl, W is OH, $NH_2$, OA, NHA or $NA_2$, A is alkyl with 1-6 C atoms, Ar is unsubstituted phenyl, phenyl which is mono- or poly- substituted by A, AO, F, CL, Br, I, $CF_3$ and-/or $NH_2$, or unsubstituted naphthyl and m, n, p, r and t are each 0, 1, 2, 3, 4 or 5, and salts thereof.

DETAILED DESCRIPTION OF THE INVENTION

It has been found that the compounds of the formula I and their salts have very useful properties. In particular, they inhibit the activity of human plasma renins. This action can be detected, for example, by the method of F. Fyhrquist et al., Clin. Chem. 22, 250–256 (1976). It is remarkable that these compounds are very specific inhibitors of renin; substantially higher concentrations of these compounds are necessary for inhibition of other aspartylproteinases (for example pepsin and cathepsin D).

The compounds can be used as medicament active compounds in human and veterinary medicine, in particular for the prophylaxis and treatment of cardiac, circulatory and vascular diseases, above all hypertension, cardiac insufficiency and hyperaldosteronism. The compounds can also be used for diagnostic purposes in order to determine the possible contribution of the renin activity towards maintenance of the pathological condition in patients with hypertension or hyperaldosteronism.

The abbreviations of amino acid radicals given above and below represent the radicals $-NH-CHR-CO-$ (wherein R has the specific meaning known for each amino acid) of the following amino acids:

Abu: 2-Aminobutyric acid
Ada: Adamantylalanine
Ala: Alanine
Arg: Arginine
Dab: 2,4-Diaminobutyric acid
Gly: Glycine
His: Histidine
Ile: Isoleucine
Leu: Leucine
tert.-Leu: tert.-Leucine
Lys: Lysine
Met: Methionine
Nbg: (2-Norbornyl)-glycine
Nle: Norleucine
N-Me-His: N-Methyl-histidine
N-Me-Phe: N-Methyl-phenylalanine
Orn: Ornithine
Phe: Phenylalanine
Pro: Proline
Ser: Serine
Thr: Threonine
Tic: 1,2,3,4-Tetrahydroquinoline-1-carboxylic acid
Trp: Tryptophan
Tyr: Tyrosine
Val: Valine.

The other abbreviations have the following meanings in the text below:

BOC: tert.-Butoxycarbonyl
CBZ: Benzyloxycarbonyl
DNP: 2,4-Dinitrophenyl
FMOC: 9-Fluorenylmethoxycarbonyl
imi-DNP: 2,4-Dinitrophenyl in the 1-position of the imidazole ring
OMe: Methyl ester
POA: Phenoxyacetyl
DCCI: Dicyclohexylcarbodiimide
HOBt: 1-Hydroxybenzotriazole.

If the abovementioned amino acids can occur in several enantiomeric forms, all these forms and also their mixtures (for example the DL-forms) are included above and below, for example as a constituent of the compounds of the formula I. The L-forms are preferred. Where individual compounds are listed below, the abbreviations of these amino acids in each case relate to the L-form, unless expressly indicated otherwise.

The compounds of the formula I include the 3,4-diamino acids of the formula I' (I; X=H; Z, E and G are absent; Y=OH):

functional derivatives thereof of the formula I" (I; Z, E and G are absent; X is only H if Y is other than OH):

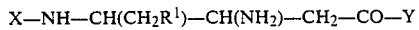

and peptides derived therefrom and functional derivatives thereof of the formula I''' (=I, but wherein at least one of the radicals Z, E and/or G is at least one amino acid radical).

If G is the group —NH—CH(CH$_2$R$^1$)—CH$_2$—CO—, the two radicals R$^1$ present in I can be identical or different.

Particularly preferred compounds of the formula I' are those which are derived from naturally occurring amino acids of the formula H$_2$N—CH(CH$_2$R$^1$)—COOH, in particular 3,4-diamino-6-methylheptanoic acid (I', R$^1$=isopropyl; "DAMH") and 3,4-diamino-5-phenylpentanoic acid (I', R$^1$=phenyl; "DAPP"), furthermore 3,4-diamino-5-cyclohexyl-pentanoic acid (I', R$^1$=cyclohexyl; "DACP"). Particularly preferred compounds of the formula I" are 3-amino-4-BOC-amino-6-methyl-heptanoic acid (I", X=BOC, R$^1$-isopropyl, Y=OH; "BOC-DAMH") and 3-amino-4-BOC-amino-5-phenylpentanoic acid (I", X=BOC, R$^1$=phenyl, Y=OH; "BOC-DAPP"), furthermore 3-amino-4-BOC-amino-5-cyclohexylpentanoic acid (I", X=BOC, R$^1$=cyclohexyl, Y=OH; "BOC-DACP").

The compounds of the formulae I, I', I" and I''', in particular DAMH and DAPP, and derivatives thereof have at least two chiral centers in the group —NH—CH(CH$_2$R$^1$)—CH(NH$_2$)—CH$_2$—CO—. They can therefore occur in various—optically inactive or optically active—forms. The formulae I, I', I" and I''' include all these enantiomeric forms. The 3S,4S-diamino enantiomers are preferred. Unless expressly indicated otherwise, the abbreviations DAMH, DAPP and DACP always relate to these 3S,4S-forms.

In the above formulae, A has 1-6, preferably 1, 2, 3 or 4, C atoms. A is preferably methyl, ethyl, propyl, isopropyl, butyl, isobutyl, sec:-butyl or tert.-butyl and furthermore also pentyl, 1-, 2- or 3-methylbutyl,, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Cycloalkyl is preferably cyclopropyl, cyclobutyl, cyclopentyl, cyclohexyl or cycloheptyl, but also, for example, 1-, 2- or 3-methylcyclopentyl or 1-, 2-, 3- or 4-methylcyclohexyl.

Ar is preferably phenyl, or furthermore o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, 2,3-, 2,4-, 2,5-, 2,6-, 3,4- or 3,5-dimethoxyphenyl, 3,4,5-trimethoxyphenyl, o-, m- or p-aminophenyl, 1- or 2-naphthyl.

R$^1$ is preferably H;, A, in particular methyl, ethyl, propyl, isopropyl, isobutyl or sec.-butyl; cyclohexyl; phenyl; p-chlorophenyl; OH; hydroxyalkyl, such as hydroxymethyl; NH$_2$; aminoalkyl, such as aminomethyl, 1- or 2-aminoethyl or 1-, 2- or 3-aminopropyl; alkoxy, such as methoxy, ethoxy, propoxy, isopropoxy or butoxy; alkoxyalkyl, such as methoxymethyl, ethoxymethyl, propoxymethyl, isopropoxymethyl, 1- or 2-methoxyethyl, 1- or 2-ethoxyethyl, 1- or 2-propoxyethyl, 1- or 2-isopropoxyethyl or 1-, 2- or 3-methoxypropyl; alkylamino, such as methylamino, ethylamino, propylamino or isopropylamino; alkylaminoalkyl, such as methylaminomethyl, ethylaminomethyl, propylaminomethyl, isopropylaminomethyl, 1- or 2-methylaminoethyl, 1- or 2-ethylaminoethyl, 1- or 2-propylaminoethyl, 1- or 2-isopropylaminoethyl or 1-, 2- or 3-methylaminopropyl; dialkylamino, such as dimethylamino, methylethylamino or diethylamino; or dialkylaminoalkyl, such as dimethylaminomethyl, methylethylaminomethyl, diethylaminomethyl, 1- or 2-dimethylaminoethyl, 1- or 2-methylethylaminoethyl, 1- or 2-dimethylaminoethyl or 1-, 2- or 3-dimethylaminopropyl. Particularly preferred radicals R$^1$ are isopropyl and phenyl, and secondly H, ethyl, OH, 2-aminoethyl and 3-aminopropyl.

R$^2$ is preferably A, in particular, methyl, ethyl, propyl, isopropyl, butyl, isobutyl or tert.-butyl; or cyclopropyl, cyclopentyl, cyclohexyl, benzyl or phenyl.

R$^3$ is preferably H, A, in particular methyl, cyclohexyl, phenyl, o-, m- or p-fluorophenyl, o-, m- or p-chlorophenyl, o-, m- or p-bromophenyl, o-, m- or p-aminophenyl, 2-, 3- or (in particular) 4-pyridyl, 1-, 2-, (in particular) 4- or 5-imidazolyl, 1-, 2-, 3- or (in particular) 4-piperidyl, N-benzyl-2-, -3- or (in particular) -4-piperidyl, or 1-, 2- or 3-piperazinyl.

X is preferably H, POA, alkoxycarbonyl, such as BOC, CBZ, alkanoyl, such as acetyl, propionyl, butyryl or isobutyryl, cycloalkylcarbonyl, such as cyclopentylcarbonyl or cyclohexylcarbonyl, aroyl, such as benzoyl, arylalkanoyl, such as phenylacetyl, 2- oder 3-phenylpropionyl, 2- or 3-o-, -m- or -p-fluorophenylpropionyl or 2- or 3-o-, -m- or -p-chlorophenylpropionyl, or cycloalkyl-alkanoyl, such as cyclohexylacetyl or 2- or 3-cyclohexylpropionyl. Particularly preferred radicals X are H, BOC and CBZ.

Z is 0 (=valency bond) or 1, preferably, however, 2 or 3 or 4 amino acid radicals bonded to one another in a peptide-like manner, in particular the groups His, Phe-His, Pro-Phe-His or His-Pro-Phe-His, or Furthermore preferably the groups Abu-His, Ada-His, Ala-His, Ala-Phe, Arg-His, Dab-His, Gly-His, His-His, Ile-His, Lev-His, tert.-Leu-his, Lvs-His, Met-His, Nbg-His, Nle-His, (N-Me-His)-His, (N-Me-Phe)-His, Orn-His, Phe-Abu, Phe-Ada, Phe-Ala, Phe-Arg, Phe-Dab, Phe-Gly, Phe-Ile, Phe-Leu, Phe-tert.-Leu, Phe-Lys, Phe-Met, Phe-Nbg, Phe-Nle, Phe-(N-Me-His), Phe-(N-Me-Phe), Phe-Orn, Phe-Phe, Phe-Pro, Phe-Ser, Phe-Ihr, Phe-Tic, Phe-Trp, Phe-Tyr, Phe-Val, Pro-His, Ser-His, Thr-His, Tic-His, Trp-His, Tyr-His, Val-His, Pro-Ala-His, Pro-Ala-Phe, Pro-Phe-Ala, Pro-Phe-Phe, His-Pro-Ala-His, His-Pro-Ala-Phe, His-Pro-Phe-Ala or His-Pro-Phe-Phe, furthermore Pro-Abu-His Pro-Ada-His, Pro-Arg-His, Pro-Dab-His, Pro-Gly-His, Pro-His-His, Pro-Ile-His, Pro-Leu-His, Pro-tert.-Leu-His, Pro-Lys-His. Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Dab, Pro-Phe-Gly, Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe Tyr, Pro-Phe-Val, Pro-Pro-His, Pro-Ser-His, Pro-Thr-His, Pro-Tic-His, Pro-Trp-His, Pro-Tyr-His, Pro-Va -His, His-Pro-Abu-His, His-Pro-Ada-His, His-Pro-Arg-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Dab, His-Pro-Phe-Gly, His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His, His-Pro-Val-His.

E is preferably absent, or is preferably Ile, or furthermore preferably Leu, and additionally Ala, Gly, Met, Ser, Thr or Val.

G is preferably absent or is preferably Phe. His or —NH—CH(CH$_2$R$^1$)—CH(NH$_2$)—CH$_2$—CO—, in particular DAMH, DAPP or DACP, and additionally Trp or Tyr.

The group —E—G— is preferably absent or is preferably Ile, Ile—NH—CH(CH$_2$R$^1$)—CH(NH$_2$)—CH$_2$—CO— or Ile-Phe, or furthermore preferably Leu-Phe, Ile-His or Leu-His.

Y is preferably OR$^3$, in particular OA, or —NH—C$_m$H$_{2m}$—R$^3$, wherein the group C$_m$H$_{2m}$ is preferably straight-chain alkylene with 1-5 C atoms, in particular —CH$_2$—, —CH$_2$CH$_2$— or —(CH$_2$)$_3$—, or furthermore also —CH$_2$)$_4$—or —(CH$_2$)$_5$—, and also, for example, —CH(CH$_3$)—, —CH(CH$_3$)—CH$_2$— or —CH$_2$—CH(CH$_3$)—. NH$_2$ is also a preferred meaning of the group —NH—C$_m$H$_{2m}$—R$^3$.

If the group G is absent, Y is preferably —NH—C$_m$H$_{2m}$—R$^3$.

The invention accordingly particularly relates to those compounds of the formula I in which at least one of the radicals mentioned has one of the abovementioned preferred meanings. Some preferred groups of compounds can be expressed by the following part formulae Ia to Ij, which correspond to the formula I, but wherein, in Ia, X is H, POA, BOC or CBA, Z is absent or is His, Phe-His, Pro-Phe-His or His-Pro-Phe-His, R$^1$ is H, ethyl, isopropyl, OH, 2-aminoethyl or 3-aminopropyl, E is absent or is Ile or Leu, G is absent or is DAMH, His or Phe, Y is OH, OMe or —NH—(CH$_2$)$_2$—R$^3$, R$^3$ is H, phenyl, pyridyl, imidazolyl or N-benzylpiperidyl and m is 0, 1 or 2; in Ib X is H, POA or BOC, Z is absent or is His, Phe-His, Pro-Phe-His or His-Pro-Phe-His, R$^1$ is H, isopropyl or phenyl, E is absent or is Ile, G is absent or is DAMH, His or Phe and Y is OH, OMe, NH$_2$, N-benzyl-4-piperidylamino or 2-phenylethylamino; in Ic X is H or BOC, Z, E and G are absent, R$^1$ is isopropyl or phenyl and Y is OH or OMe;

in Id:
(a) Z is 3 or 4 amino acid radicals bonded to one another in a peptide-like manner selected from the group consisting of Abu, Ada, Ala, Arg, Dab, Gly, His, Ile, Leu, tert.-Leu, Lys, Met, Nbg, Nle, N-Me-His, N-Me-Phe, Orn, Phe, Pro-Ser, Thr, Tic, Trp, Tyr and Val, and/or
(b) G is —NH—CH(CH$_2$R$^1$)—CH(NH$_2$)—CH$_2$—CO—, and/or
(c) R$^1$ is —C$_p$H$_{2p}$—W and W is OA, NHA or NA$_2$, and/or (d) Y is —O—C$_m$H$_{2m}$—R$^3$ or —NH—C$_m$H$_{2m}$—R$^3$, m is 2, 3, 4 or 5 R$^3$ is pyridyl, imidazolyl, piperidyl, N-benzyl-piperidyl or piperazinyl;

in Ie: Z is 3 or 4 amino acid radicals bonded to one; another in a peptide-like manner selected from the group consisting of Abu, Ada, Ala, Arg, Dab, Gly, His, Ile, Leu, tert.-Leu, Lys, Met, Nbg, Nle, N-Me-His, N-Me-Phe, Orn, Phe, Pro-Ser, Thr, Tic, Trp, Tyr and Val;

in If: G is —NH—CH(CH$_2$R$^1$)—CH(NH$_2$)—CH$_2$CO—;

in Ig: Z is 3 or 4 amino acid radicals bonded to; one another in a peptide-like manner selected from the group consisting of His, Phe and Pro;

in Ih: Z is Pro-Phe-His or His-Pro-Phe-His;

in Ii: G is DAMH, DAPP or DACP;

in Ij: G is DAMH.

The invention furthermore relates to a process for the preparation of a diamino acid derivative of the formula I and of its salts, characterised in that it is Liberated from one of its functional derivatives by treatment with a solvolyzing or hydrogenolyzing agent, or in that an amino-keto acid derivative of the formula II

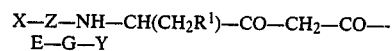

wherein R$^1$, E, G, X, Y and Z have the meaning given in the case of formula I, is subjected to reductive amination, and in that, if appropriate, a functionally modified amino and/or hydroxyl group in a compound of the formula I is Liberated by treatment with solvolyzino or hydrogenoly zing agents, and/or a compound of the formula I is converted into one of its salts by treatment with an acid or base.

The compounds of the formula I and also the starting substances for their preparation are otherwise prepared by methods which are known per se, such as are described in the Literature (for example in standard works such as Houben-Weyl, Methoden der Organischen Chemie (Methods of organic chemistry), Georg-Thieme-Verlag, Stuttgart; and furthermore European Patent Application No. 45,665, European Patent Application No. 77,028, European Patent Application No. 77,029 and European Patent Application No. 81,783), and in particular under reaction conditions which are known and suitable for the reactions mentioned. It is also possible to utilize variants which are known per se and are not mentioned here in more detail.

If desired, the starting substances can also be formed in situ, so that they are not isolated from the reaction mixture but are immediately reacted further to give the compounds of the formula I.

The compounds of the formula I are preferably obtained by a process in which they are liberated from their functional derivatives by solvolysis, in particular hydrolysis, or by hydrogenolysis.

Preferred starting substances for the solvolysis or hydrogenolysis are those which contain corresponding protected-amino and/or hydroxyl groups instead of one or more free amino and/or hydroxyl groups, preferably those which carry an amino-protective group instead of an H atom which is bonded to an N atom, in particular those of the formula III

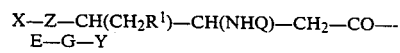

wherein Q is an amino-protective group.

Starting substances which carry a hydroxyl-protective group instead of the H atom of a hydroxyl group are furthermore preferred.

It is also possible for several—identical or different—protected amino and/or hydroxyl groups to be present in the molecule of the starting substance. If the protective groups present differ, they can in many cases be split off selectively.

The expression "amino-protective group" is generally known and relates to groups which are suitable for protecting (blocking) an amino group from chemical reactions but which can easily be removed after the desired chemical reaction has been carried out at other sites of the molecule. Typical groups of this type are, in particular, unsubstituted or substituted acyl groups, and furthermore unsubstituted or substituted aryl (for example 2,4-dinitrophenyl) or aralkyl (for example benzyl, 4-nitrobenzyl or triphenylmethyl) groups. Since the amino-protective groups are removed after the desired reaction (or reaction sequence), their nature and size is otherwise not critical; however, those with 1-20, in particular 1-8, C atoms are preferred. The expression "acyl group" needs to be interpreted in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and, above all, aralkoxycarbonyl groups. Examples of such acyl groups are alkanoyl, such as acetyl, propionyl and butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl, 2,2,2-trichloroethoxycarbonyl, BOC and 2-iodoethoxycarbonyl; and aralkyloxycarbonyl, such as CBZ ("carbobenzoxy"), 4-methoxybenzyloxycarbonyl and FMOC. Preferred acyl groups are CBZ, FMOC, benzyl and acetyl.

The expression "hydroxy-protective group" is also generally known and relates to groups which are suitable for protecting a hydroxyl group from chemical reactions but which can easily be removed after the desired chemical reaction has been carried out at other sites of the molecule. Typical groups of this type are the abovementioned unsubstituted or substituted aryl, aralkyl or acyl groups, and furthermore also alkyl groups. The nature and size of the hydroxy-protective groups is not critical, since they are removed again after the desired chemical reaction or reaction sequence; groups with 1-20, in particular 1-10, C atoms are preferred. Examples of hydroxy-protective groups, are, inter alia, benzyl, p-nitrobenzoyl, p-toluenesulfonyl and acetyl, benzyl and acetyl being particularly preferred.

The functional derivatives of the compounds of the formula I to be used as starting substances can be prepared by the customary methods of amino acid and peptide synthesis, such as are described, for example, in the standard works and patent applications mentioned.

The liberation of the compounds of the formula I from their functional derivatives is effected—depending on the protective group used—with, for example, strong acids, advantageously with trifluoroacetic acid or perchloric acid, and also with other strong inorganic acids, such as hydrochloric acid or sulfuric acid, strong organic carboxylic acids, such as trichloroacetic acid, or sulfonic acids, such as benzene- or p-toluene-sulfonic acid. The presence of an additional inert solvent is possible but not always necessary. Preferred suitable inert solvents are organic solvents, for example carboxylic acids, such as acetic acid, ethers, such as tetrahydrofuran or dioxane, amides, such as dimethylformamide (DMF), halogenated hydrocarbons, such as methylene chloride, and furthermore also alcohols, such as methanol, ethanol or isopropanol, and water. Mixtures of the abovementioned solvents can furthermore be used. Trifluoroacetic acid is preferably used in excess, without the addition of a further solvent, and perchloric acid is used in the form of a mixture of acetic acid and 70% perchloric acid in a ratio of 9:1. The reaction temperatures for the splitting reaction are advantageously between about 0° and about 50°, and the reaction is preferably carried out between 15° and 30° (room temperature).

The BOC group can preferably be split off, for example, with 40% trifluoroacetic acid in methylene chloride or with about 3 to 5 N HCL in dioxane at 15°-30°, and the FMOC group can be split off with an approximately 5 to 20% solution of dimethylamine, diethylamine or piperidine in DMF at 15°-30°. The DNP group can also be split off, for example, with an approximately 3 to 10% solution of 2-mercaptoethanol in DMF/water at 15°-30°.

Protective groups which can be removed hydrogenolytically (for example CBZ or benzyl) can be split off, for example, by treatment with hydrogen in the presence of a catalyst, (for example a noble metal catalyst, such as palladium, advantageously on a support, such as charcoal). Suitable solvents here are those mentioned above, in particular, for example, alcohols, such as methanol or ethanol, or amides, such as DMF. The hydrogenolysis is as a rule carried out at temperatures between about 0° and 100° under pressures between about 1 and 200 bar, preferably at 20°-30° under 1-10 bar. Hydrogenolysis of the CBZ group is readily effected, for example, on 5-10% Pd-C in methanol at 20°-30°.

The compounds of the formula I can also be prepared by reductive amination of amino-keto acid derivatives of the formula II.

These are obtainable, for example, from amino acids of the formula X—Z—NH—CH(CH$_2$R$^1$)—COOH by conversion into the corresponding imidazolides with carbonyldiimidazole and subsequent reaction with malonic acid derivatives of the formula HOOC—CH$_2$—CO—E—G—Y or salts thereof.

The reductive amination can be carried out in one or several stages. First, the compound II can be treated with ammonium salts, for example ammonium acetate, and NaCNBH$_3$, preferably in an inert solvent, for example an alcohol, such as methanol, at temperatures between about 0° and 50°, in particular between 15° and 30°.

It is furthermore possible first to convert the ketone II into the oxime with hydroxylamine in the customary manner and to reduce this oxime to the amine, for example by catalytic hydrogenation on Raney nickel.

If desired, a functionally modified amino and/or hydroxyl group in a compound of the formula I can be liberated by solvolysis or hydrogenolysis by one of the methods described above.

Thus, in particular, a compound of the formula I wherein X is other than H can be converted into a compound of the formula I (X=H) advantageously by hydrogenolysis, If X is BOC, the BOC group can be split off, for example, with HCL in dioxane at room temperature.

It is furthermore possible, for example, to hydrolyse an ester of the formula I ($Y=O-C_mH_{2m}R^3$) to the corresponding acid of the formula I ($Y=OH$), for example with aqueous-dioxanic sodium hydroxide solution at room temperature.

A base of the formula I can be converted into the associated acid addition salt with an acid. Acids which give physiologically acceptable salts are particularly suitable for this reaction. Thus, it is possible to use inorganic acids, for example sulfuric acid, nitric acid, hydrogen halide acids, such as hydrochloric acid or hydrobromic acid, phosphoric acids, such as orthophosphoric acid and sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sultonic acid, ethanedisulfonic acid, 2-hydroxyethanesulfonic acid, benzenesulfonic acid, p-toluenesulfonic acid, naphthalenemono- and -di-sulfonic acids and laurylsulfuric acid. Salts with physiologically unacceptable acids, for example picrates, can be used to isolate and/or purify compounds of the formula I.

An acid of the formula I can be converted into one of its physiologically acceptable metal or ammonium salts by reaction with a base. Possible salts are, in particular, sodium, potassium, magnesium, calcium and ammonium salts, and furthermore substituted ammonium salts, for example the dimethyl-, diethyl- or diisopropyl-ammonium, ammonium, monoethanol-, diethanol- and triethanol-ammonium, cyclohexylammonium, dicyclohexylammonium and dibenzyl-ethylenediammonium salts, and moreover, for example, salts with N-methyl-D-glucamine or with basic amino acids, such as arginine or lysine.

The new compounds of the formula I and their physiologically acceptable salts can be used to prepare pharmaceutical products by a process in which they are brought into a suitable dosage form together with at least one excipient or auxiliary and, if desired, together with one or more other active compound(s). The formulations thus obtained can be employed as medicaments in human or veterinary medicine. Possible excipients are organic or inorganic substances which are suitable for enteral (for example rectal) or parenteral administration or for administration in the form of an inhalation spray and do not react with the new compounds, for example water, vegetable oils, benzyl alcohols, polyethylene glycols, glycerol triacetate and other fatty acid glycerides, gelatin and soya lecithin. Suppositories are used for rectal administration and solutions, preferably oily or aqueous solutions, and furthermore suspensions, emulsions or implants are used for parenteral administration. Sprays which contain the active compound either dissolved or suspended in a propellant gas mixture (for example fluoro-chloro-hydrocarbons) can be used for administration as an inhalation spray. The active compound is advantageously used here in micronized form, it being possible for one or more additional physiologically acceptable solvents, for example ethanol, to be present. Inhalation solutions can be administered with the aid of customary inhalers. The new compounds can also be lyophilized and the resulting lyophilizates can be used, for example, for the preparation of injection products. The formulations mentioned can be sterilized and/or can contain auxiliaries, such as preservatives, stabilizers and/or wetting agents, emulsifiers, salts for influencing the osmotic pressure, buffer substances, colorants and/or aroma substances. If desired, they can also contain one or more other active compounds, for example one or more vitamins.

The substances according to the invention are as a rule administered analogously to other known commercially available peptides, for each of the uses mentioned above, and in particular analogously to the compounds described in European Patent Application No. 77,028, preferably in dosages of about 100 mg to 30 g, in particular about 500 mg to 5 g, per dosage unit. The daily dosage is preferably about 2 to 600 mg/kg of body weight. For example, renin-associated hypertension and hyperaldosteronism are effectively treated by administration of from 10 mg to 300 mg/kg of body weight. For diagnostic purposes, the novel peptides may be administered in a single dose of from 0.1 to 10 mg/kg of body weight.

The specific dose for each particular patient depends, however, on the most diverse factors, for example on the efficacy of the particular compound employed, the age, body weight, general state of health, sex, diet, time and mode of administration, rate of excretion, medicament combination and severity of the particular disease to which the therapy applies. Parenteral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the following examples, "customary working up" means: water is added, if necessary, the mixture is extracted with ether or methylene chloride, the organic phase is separated off, dried with sodium sulfate, filtered and evaporated and the residue is purified by chromatography on silica gel and/or crystallization.

EXAMPLE 1

4.6 g of NaCNBH$_3$ are added to a solution of 28.7 g of methyl 3-oxo-4S-BOC-amino-6-methylheptanoate and 77 g of ammonium acetate in 500 ml of methanol and the mixture is stirred at 20° for 12 hours. The excess NaCNBH$_3$ is hydrolysed by addition of 1 N HCL to pH 2. The pH is brought to 9 with sodium hydroxide solution and the mixture is worked up in the customary manner. Methyl 3S-amino-4S-BOC-amino-6-methylheptanoate (m.p. 88°) and methyl 3R-amino-4S-BOC-amino-6-methylheptanoate (m.p. 97°) are obtained by chromatography on silica gel (methylene chloride/ethyl acetate/methanol).

The following compounds are obtained analogously by reductive amination of the corresponding 3-oxo-4S-BOC-amino esters:

3S-Methylamino-4S-BOC-amino-5-cyclohexylpentanoate

3R-Methylamino-4S-BOC-amino-5-cyclohexylpentanoate

3S-Methylamino-4S-BOC-amino-5-phenylpentanoate

3R-Methylamino-4S-BOC-amino-5-phenylpentanoate
Methyl 3S-amino-4S-BOC-amino-5-p-chlorophenylpentanoate
Methyl 3R-amino-4S-BOC-amino-5-p-chlorophenylpentanoate
Methyl 3S-amino-4S-BOC-amino-pentanoate
Methyl 3R-amino-4S-BOC-amino-pentanoate
Methyl 3S-amino-4S-BOC-amino-hexanoate
Methyl 3R-amino-4S-BOC-amino-hexanoate
Methyl 3S-amino-4S-BOC-amino-8-CBZ-amino-octanoate
Methyl 3R-amino-4S-BOC-amino-8-CBA-amino-octanoate
Methyl 3S-amino-4S-BOC-amino-5-hydroxypentanoate
Methyl 3R-amino-4S-BOC-amino-5-hydroxypentanoate
Methyl 3S-amino-4S-BOC-amino-5-methoxypentanoate
Methyl 3R-amino-4S-BOC-amino-5-methoxypentanoate
Methyl 3S-amino-4S-BOC-amino-5-ethylaminopentanoate
Methyl 3R-amino-4S-BOC-amino-5-ethylaminopentanoate
Methyl 3S-amino-4S-BOC-amino-5-dimethylaminopentanoate
Methyl 3R-amino-4S-BOC-amino-5-dimethylaminopentanoate.

EXAMPLE 2

A solution of 37.8 g of methyl 3-benzylamino-4S-BOC-amino-6-methyl-heptanoate (obtainable by stirring methyl 4S-BOC-amino-6-methyl-2-heptanoate with excess benzylamine at 0° for 48 hours) in 250 ml of ethanol is hydrogenated over 10 g of 5% palladium hydroxide-on-charcoal at 20° under 1 bar for 8 hours. The mixture is filtered and the filtrate is evaporated to give methyl 3S-amino- (m.p. 88°) and 3R-amino-4S-BOC-amino-6-methylheptanoate (m.p. 97°), which are separated on silica gel (methylene chloride/ethyl acetate/methanol).

EXAMPLE 3

140 ml of 2 N sodium hydroxide solution are added to a solution of 28.8 g of methyl 3S-amino-4S-BOC-amino-6-methyl-heptanoate in 140 ml of dioxane and the mixture is stirred at 20° for 2 hours. It is then brought to pH 6 and the resulting 3S-amino-4S-BOC-amino-6-methyl-heptanoic acid ("BOC-DAMH") is filtered off (m.p. 221°-222°).

3R-Amino-4S-BOC-amino-6-methyl-heptnaoic acid, m.p. 248°-250°, is obtained analogously from the 3R,4S-epimer.

The following compounds are obtained by hydrolysis:
3S-Amino-4S-BOC-amino-5-cyclohexylpentanoic acid
3R-Amino-4S-BOC-amino-5-cyclohexylpentanoic acid
3S-Amino-4S-BOC-amino-5-phenylpentanoic acid ("BOC-DAPP"), m.p. 214°-215°
3R-Amino-4S-BOC-amino-5-phenylpentanoic acid
3S-Amino-4S-BOC-amino-5-p-chlorophenylpentanoic acid
3R-Amino-4S-BOC-amino-5-p-chlorophenylpentanoic acid
3S-Amino-4S-BOC-amino-pentanoic acid
3R-Amino-4S-BOC-amino-pentanoic acid
3S-Amino-4S-BOC-amino-hexanoic acid
3R-Amino-4S-BOC-amino-hexanoic acid
3S-Amino-4S-BOC-amino-8-CBZ-amino-octanoic acid
3R-Amino-4S-BOC-amino-8-CBZ-amino-octanoic acid
3S-Amino-4S-BOC-amino-5-hydroxypentanoic acid
3R-Amino-4S-BOC-amino-5-hydroxypentanoic acid
3S-Amino-4S-BOC-amino-5-methoxypentanoic acid
3R-Amino-4S-BOC-amino-5-methoxypentanoic acid
3S-Amino-4S-BOC-amino-5-ethylaminopentanoic acid
3R-Amino-4S-BOC-amino-5-ethylaminopentanoic acid
3S-Amino-4S-BOC-amino-5-dimethylaminopentanoic acid
3R-Amino-4S-BOC-amino-5-dimethylaminopentanoic acid.

EXAMPLE 4

A solution of 276 mg of BOC-DAMH in 5 ml of 4 N HCL in dioxane is stirred at 20° for 30 minutes and then evaporated. 3S,4S-Diamino-6-methylheptanoic acid ("DAMH"), dihydrochloride, m.p. 136°-138°, is obtained.

3R,4S-diamino-6-methylheptanoic acid dihydrochloride is obtained analogously from the 3R,4S-epimer.

The following compounds are obtained analogously by splitting of the corresponding 4-BOC—NH derivatives:
3S,4S-Diamino-5-cyclohexylpentanoic acid ("DACP")
3R,4S-Diamino-5-cyclohexylpentanoic acid
3S,4S-Diamino-5-phenylpentanoic acid ("DAPP"), dihydrochloride, m.p. 138°-140°
3R,4S-Diamino-5-phenylpentanoic acid
3S,4S-Diamino-5-chlorophenylpentanoic acid
3R,4S-Diamino-5-chlorophenylpentanoic acid
3S,4S-Diaminopentanoic acid
3R,4S-Diaminopentanoic acid
3S,4S-Diaminohexanoic acid
3R,4S-Diaminohexanoic acid
3S,4S-Diamino-8-CBZ-amino-octanoic acid
3R,4S-Diamino-8-CBZ-amino-octanoic acid
3S,4S-Diamino-5-hydroxypentanoic acid
3R,4S-Diamino-5-hydroxypentanoic acid
3R,4S-Diamino-5-hydroxypentanoic acid
3S,4S-Diamino-5-methoxypentanoic acid
3R,4S-Diamino-5-methoxypentanoic acid
3S,4S-Diamino-5-ethylaminopentanoic acid
3R,4S-Diamino-5-ethylaminopentanoic acid
3S,4S-Diamino-5-dimethylaminopentanoic acid
3R,4S-Diamino-5-dimethylaminopentanoic acid.

EXAMPLE 5

1.2 g of 3S-FMOC-amino-4S-(BOC-L-phenylalanyl-L-histidyl-amino)-6-methyl-heptanoyl-L-isoleucyl-N-(1-benzyl-4-piperidyl)-amide [m.p. 187°-189°; obtainable by reaction of BOC-Ile-OH with 1-benzyl-4-aminopiperidine/DCCI/HOBt to give BOC-Ile-N-(1-benzyl-4-piperidyl)-amide (m.p. 127°-128°), hydrolysis with 4 N HCl/dioxane to give Ile-N-(1-benzyl-4-piperidyl)-amide (m.p. 219°-221°), reaction with 3S-FMOC-amino-4S-BOC-amino-6-methyl-heptanoic acid (m.p. 115°-117°; obtainable from 3S-amino-4S-BOC-amino-6-methylheptanoic acid and FMOC chloride)/DCCI/HOBt to give 3S-FMOC-amino-4S-BOC-amino-6-methylheptanoyl-Ile-N-(1-benzyl-4-piperidyl)-amide (m.p. 208°, decomposition), hydrolysis with 4 N HCt/dioxane to give 3S-FMOC-amino-4S-amino-6-methyl-heptanoyl-Ile-N-(1-benzyl-4-piperidyl)-amide hydrochloride (m.p. 176°, decomposition), reaction with BOC-(imi-DNP)-His-OH/DCCI/HOBt to give 3S-FMOC-4S-[BOC-(imi-DNP)-His—NH]-6-methylheptanoyl-Ile-N-(1-benzyl-4-piperidyl)-amide (m.p. 198°, decomposition), hydrolysis with 4 N HCl/dioxane to give 3S-FMOC-amino-4S-[(imi-DNP)-His—NH]-6-methyl-heptanoyl-Ile-N-(1-benzyl-4-piperidyl)-amide hydrochloride (m.p. 225°, decomposition), reaction with BOC-Phe-OH/DCCI/HOBt to give 3S-FMOC-amino-4S-[BOC-Phe-(imi-DNP)-His—NH]-6-methyl-heptanoyl-Ile-N-(1-benzyl-4-piperidyl)-amide (m.p. 185°) and stirring for 2 hours with mercaptoethanol in DMF/water 1:1 at pH 8] are dissolved in 50 ml of a 10% solution of dimethylamine in DMF, the solution is stirred at 20° for 30 minutes and evaporated and the residue is chromatographed on silica gel with methylene chloride/methanol/acetone to give 3S-amino-4S-(BOC-L-phenylalanyl-L-histidyl-amino)-6-methyl-heptanoyl-L-isoleucyl-N-(1-benzyl-4-piperidyl)-amide ["BOC-Phe-His-DAMH-Ile-N-(1-benzyl-4-piperidyl)-amide"], m.p. 175°–176°.

The following compounds are obtained analogously by splitting the corresponding 3S-FMOC-amino derivatives:
POA-His-DAMH-Ile-Phe-OMe, m.p. 160°–162°
BOC-Pro-Phe-His-DAMH-Ile-Phe-OMe, m.p. 104°–106°
BOC-Phe-His-DAMH-Ile-Phe-OMe, m.p. 181°–183°
BOC-His-His-DAMH-Ile-Phe-OMe
BOC-Tyr-His-DAMH-Ile-Phe-OMe
BOC-Trp-His-DAMH-Ile-Phe-OMe
BOC-Pro-His-DAMH-Ile-Phe-OMe
CBZ-Phe-His-DAMH-Ile-Phe-OMe
CBZ-Phe-His-DAMH-Ile-N-(2-phenylethyl-amide), m.p. 192°–194°
CBZ-His-DAMH-Ile-Phe-OMe.

EXAMPLE 6

70 mg of hydroxylamine hydrochloride are added to a solution of 773 mg of 3-oxo-4S-(BOC-L-phenylalanyl-L-histidyl—NH)-6-methylheptanoyl-L-isoleucyl-N-(2-phenylethyl)-amide and 1.43 g of $Na_2CO_3 \cdot 10H_2O$ in 5 ml of methanol and 5 ml of water and the mixture is stirred at 20° for 14 hours. The oxime precipitated is filtered off with suction, dried, dissolved in 10 ml of methanol and hydrogenated over 0.5 g of Raney Ni at 20° under 5 bar. The mixture is filtered, the filtrate is evaporated and the residue is separated on silica gel (methylene chloride/methanol/acetic acid/water) to give 3S-amino-4S-(BOC-L-phenylalanyl-L-histidyl—NH)-6-methyl-heptanoyl-L-isoleucyl-N-(2-phenylethyl)-amide ("BOC-Phe-His-DAMH-Ile-2-phenylethylamide"; m.p. 180°–182°) and 3R-amino-4S-(BOC-Phe-His—NH)-6-methylheptanoyl-Ile-N-(2-phenylethyl)-amide.

EXAMPLE 7

A solution of 831 mg of 3-oxo-4S-(BOC-Phe-His—NH)-6-methyl-heptanoyl-Ile-Phe-OMe and 250 mg of benzylamine in 10 ml of ethanol is stirred at 20° for 16 hours. After addition of 0.5 g of Pd-charcoal (5%), the resulting Schiff's base is hydrogenated at 20° under 1 bar for 8 hours. After one equivalent of $H_2$ has been taken up, the mixture is filtered, the filtrate is evaporated, the resulting diastereoisomer mixture of the two 3-benzylamino compounds is dissolved in 5 ml of 50% ethanol, 0.5 g of palladium hydroxide-on-charcoal is added and hydrogenation is again carried out at 20° under 1 bar for 16 hours. After filtration, evaporation and fractional recrystallization from ethanol, 3S-amino-4S-(BOC-Phe-His—NH)-6-methylheptanoyl-Ile-Phe-OMe ("BOC-Phe-His-DAMH-Ile-Phe-OMe"; m.p. 181°–183°) and 3R-amino-4S-(BOC-Phe-His—NH)-6-methylheptanoyl-Ile-Phe-OMe are obtained.

The following compounds are obtained analogously from the corresponding 3-oxo compounds:
BOC-Phe-His-DAMH-Val-Phe-OMe
BOC-Phe-His-DAMH-Gly-Phe-OMe
BOC-Phe-His-DAMH-Thr-Phe-OMe
BOC-Phe-His-DAMH-Leu-Phe-OMe
BOC-Phe-His-DAMH-Ala-Phe-OMe
BOC-Phe-His-DAMH-Met-Phe-OMe
BOC-Phe-His-DAMH-Ser-Phe-OMe
BOC-Phe-His-DAMH-Ile-Tyr-OMe
BOC-Phe-His-DAMH-Ile-His-OMe
BOC-Phe-His-DAMH-Ile-Trp-OMe.

EXAMPLE 8

A solution of 863 mg of oily 3S-benzylamino-4S-(BOC-Phe-His—NH)-6-methyl-heptanoyl-Ile-(2-phenylethylamide) [obtainable by reaction of 4S-(BOC-Phe-His—NH)-6-methyl-2-heptenoyl-Ile-N-(2-phenylethylamide) with benzylamine at 0°° in 10 ml of methanol is hydrogenated over 0.5 g of palladium hydroxide-on-charcoal at 20° under 1 bar until the uptake of $H_2$ has ended. The mixture is filtered and the filtrate is evaporated to give BOC-Phe-His-DAMH-Ile-(2-phenylethylamide), m.p. 180°–182°.

EXAMPLE 9

1 g of 3S-CBZ-amino-4S-(POA-His-amino)-5-phenyl-pentanoyl-Ile-Phe-OMe [obtainable by reaction of BOC-DAPP-OMe with benzyloxycarbonyl chloride to give methyl 3S-CBZ-amino-4S-BOC-amino-5-phenyl-pentanoate (m.p. 111°–112°), hydrolysis to give 3S-CBZ-amino-4S-BOC-amino-5-phenyl-pentanoic acid (m.p. 126°–127°), reaction with H-Ile-Phe-OMe to give 3S-CBZ-amino-4S-BOC-amino-5-phenylpentanoyl-Ile-Phe-OMe and reaction with POA-His-OH] is dissolved in 10 ml of methanol and hydrogenated over 0.5 g of 10% Pd-C at 20° under 1 bar for 3 hours, the mixture is filtered and the filtrate is evaporated to give POA-His-DAPP-Ile-Phe-OMe, m.p. 113°–115°.

The following compounds are obtained analogously by hydrogenolysis of the corresponding CBZ derivatives:
3R-Amino-4S-(POA-His—NH)-5-phenyl-pentanoyl-Ile-Phe-OMe [obtainable via methyl 3R-CBZ-amino-4S-BOC-amino-5-phenylpentanoate (m.p. 159°–160°)]
BOC-Phe-His-DAMH-Ile-Phe—NH₂, m.p. 175° [decomposition; obtainable via methyl 3S-CBZ-amino-4S-BOC-amino-6-methylheptanoate (m.p. 67°–68°) and 3S-CBZ-amino-4S-BOC-amino-6-methyl-heptanoic acid (m.p. 118°–120°)]
3R-Amino-4S-(BOC-Phe-His—NH)-6-methyl-heptanoyl-Ile-Phe—NH₂ [obtainable via methyl 3R-CBZ-amino-4S-BOC-amino-6-methyl-heptanate (m.p. 146°–148°) and 3R-CBZ-amino-4S-BOC-amino-6-methyl-heptanoic acid]
BOC-Phe-His-DAPP-Ile-Phe-OMe, m.p. 180°–181°
BOC-Phe-His-DAMH-Ile-His-OMe
BOC-His-Pro-Phe-His-DAMM-Ile-Phe—NH₂, m.p. 150° (decomposition)
BOC-Phe-His-DAMH-Leu-Phe-OMe
BOC-His-Pro-Phe-His-DAMH-Ile-His-OMe
BOC-Phe-His-DAMH-Ile-His—NH₂
BOC-Phe-His-DAMH-Leu-PHe—NH₂

BOC-His-Pro-His-DAMH-Leu-Phe—NH₂
BOC-His-Pro-Phe-His-DAMH-Leu-Tyr—NH₂
BOC-Ala-His-DAMH-Ile-Phe-OMe
BOC-Arg-His-DAMH-Ile-Phe-OMe
BOC-Gly-His-DAMH-Ile-Phe-OMe
BOC-His-His-DAMH-Ile-Phe-OMe
BOC-Ile-His-DAMH-Ile-Phe-OMe
BOC-Leu-His-DAMH-Ile-Phe-OMe
BOC-Lys-His-DAMH-Ile-Phe-OMe
BOC-Met-His-DAMH-Ile-Phe-OMe
BOC-Orn-His-DAMH-Ile-Phe-OMe
BOC-Pro-His-DAMH-Ile-Phe-OMe
BOC-Ser-His-DAMH-Ile-Phe-OMe
BOC-Thr-His-DAMH-Ile-Phe-OMe
BOC-Val-His-DAMH-Ile-Phe-OMe
BOC-Phe-His-DAMH-Ile-Phe-OMe, m.p. 181°–183°
BOC-Phe-Phe-DAMH-Ile-Phe-OMe
BOC-Phe-Tyr-DAMH-Ile-Phe-OMe
BOC-Phe-Trp-DAMH-Ile-Phe-OMe
BOC-Phe-Lys-DAMH-Ile-Phe-OMe
BOC-Phe-Orn-DAMH-Ile-Phe-OMe
BOC-Phe-Arg-DAMH-Ile-Phe-OMe
BOC-Phe-His-DAMH-Ile-N-(2-cyclohexylethyl)-amide
BOC-Phe-His-DAMH-Ile-N-benzylamide
BOC-Phe-His-DAMH-Ile-N-(2-phenylethyl)-amide
BOC-Phe-His-DAMH-Ile-N-(3-phenylpropyl)-amide, m.p. 158° (dec.)
BOC-Phe-His-DAMH-Ile-N-(5-p-tolyl-pentyl)-amide
BOC-Phe-His-DAMH-Ile-N-(2-p-methoxyphenylethyl)-amide
BOC-Phe-His-DAMH-Ile-N-[2-(3,4-dimethoxyphenyl)-ethyl]-amide
BOC-Phe-His-DAMH-Ile-N-(2-p-fluorophenylethyl)-amide
BOC-Phe-His-DAMH-Ile-N-(2-p-chlorophenylethyl)-amide
BOC-Phe-His-DAMH-Ile-N-(2-o-iodophenylethyl)-amide
BOC-Phe-His-DAMH-Ile-N-(2-m-trifluoromethylphenylethyl)-amide
BOC-Phe-His-DAMH-Ile-N-(2-p-aminophenylethyl)-amide
BOC-Phe-His-DAMH-Ile-N-(4-pyridylmethyl)-amide
BOC-Phe-His-DAMH-Ile-N-[2-(4-imidazolyl)-ethyl]-amide
BOC-Phe-His-DAMH-Ile-N-(4-piperidyl)-amide
BOC-Phe-His-DAMH-Ile-N-(4-piperidylmethyl)-amide
BOC-Phe-His-DAMH-Ile-N-[2-(1-piperazinyl)-ethyl]-amide
Acetyl-Phe-His-DAMH-Ile-Phe-OMe
Acetyl-Pro-Phe-His-DAMH-Leu-Phe—NH₂
Acetyl-Phe-His-DAMH-Leu-Phe—NH₂
Isobutyryl-His-Pro-Phe-His-DAMH-Ala-Phe—NH₂
Isobutyryl-Phe-His-DAMH-Ile-Phe-OMe
Isobutyryl-His-Pro-Phe-His-DAMH-Ile-His—NH₂
Isovaleryl-His-Pro-Phe-His-DAMH-Ile-His—NH₂
Isovaleryl-His-Pro-Phe-His-DAMH-Leu-His—NH₂
Isovaleryl-His-Pro-Phe-His-DAMH-Leu-Phe—NH₂
Benzoyl-His-DAMH-Ile-Phe-OMe
Phenylacetyl-His-DAMH-Ile-Phe-OMe
α-Naphthylacetyl-His-DAMH-Ile-Phe—NH₂, m.p. 224°–226°
3-Phenylpropionyl-His-DAMH-Ile-Phe-OMe
3-p-Tolylpropionyl-His-DAMH-Ile-Phe-OMe
3-o-Methoxyphenylpropionyl-His-DAMH-Ile-Phe-OMe
3-p-Methoxyphenylpropionyl-His-DAMH-Ile-Phe-OMe
3-p-Fluorophenylpropionyl-His-DAMH-Ile-Phe-OMe
3-p-Chlorophenylpropionyl-His-DAMH-Ile-Phe-OMe
3-p-Bromophenylpropionyl-His-DAMH-Ile-Phe-OMe
3-p-Iodophenylpropionyl-His-DAMH-Ile-Phe-OMe
3-m-Trifluoromethylphenylpropionyl-His-DAMH-Ile-Phe-OMe
3-Cyclohexylpropionyl-His-DAMH-Ile-Phe-OMe
6-Cycloheptylhexanoyl-His-DAMH-Ile-Phe-OMe
POA-His-DAMH-Ile-Phe-OMe
Cyclopropylcarbonyl-Phe-His-DAMH-Phe-OMe
Cyclopentylcarbonyl-Phe-His-DAMH-Ile-Phe-OMe
Cyclohexylcarbonyl-Phe-His-DAMH-Ile-Phe-OMe
3S-Amino-4S-BOC-Phe-His-amino-pentanoyl-Ile-Phe-OMe [m.p. 179°–180° (dec.); obtainable via methyl 3S-CBZ-amino-4S-BOC-aminopentanoate (m.p. 140°) and 3S-CBZ-amino-4S-BOC-aminopentanoic acid (oil; rf 0.18 on silica gel with dichloromethane/methanol 9:1)]
3R-Amino-4S-BOC-Phe-His-amino-pentanoyl-Ile-Phe-OMe [obtainable via methyl 3R-CBZ-amino-4S-BOC-aminopentanoate (m.p. 138°–139°)]
3S-Amino-4S-BOC-Phe-His-amino-5-hydroxypentanoyl-Ile-Phe-OMe
3S, 8-Diamino-4S-BOC-Phe-His-amino-octanoyl-Ile-Phe-OMe [obtainable via methyl 3S, 8-bis-(CBZ-amino)-4S-BOC-aminooctanoate (m.p. 101°–102°) and 3S, 8-bis-(CBZ-amino)-4S-BOC-aminooctanoic acid (m.p. 201°–203°)]
3R, 8-Diamino-4S-BOC-Phe-His-amino-octanoyl-Ile-Phe-OMe [obtainable via methyl 3R, 8-bis-(CBZ-amino)-4S-BOC-aminooctanoate (m.p. 137°–138°) and 3R, 8-bis-(CBZ-amino)4S-BOC-aminooctanoic acid (m.p. 201°–203°)]
Benzoyl-His-DAMH-Ile-DAMH-OMe
Phenylacetyl-His-DAMH-Ile-DAMH-OMe
Phenoxyacetyl-His-DAMH-Ile-DAMH-OMe
3-Phenylpropionyl-His-DAMH-Ile-DAMH-OMe
2-Benzyl-3-phenylpropionyl-His-DAMH-Ile-DAMH-OMe
BOC-Phe-His-(3R,4S)-DAMH-Ile-Phe-OMe, m.p. 140°–143°
BOC-Phe-His-DAMH-tert.-Leu-Phe-OMe, m.p. 141°–142°
BOC-Pro-Phe-His-DAMH-Ile-N-(2-phenylethylamide), formiate, m.p. 125° (dec.)
BOC-His-Pro-Phe-His-DAMH-Ile-N-(2-phenylethylamide), acetate, m.p. 169° (dec.)
BOC-Phe-His-DAMH-Ile-N-(2-(4-pyridyl)-amide), acetate, m.p. 135°
BOC-Phe-His-DAMH-Ile-N-(2-(3,4-dimethoxyphenyl)-ethylamide), m.p. 168°–170°
BOC-Phe-His-DAMH-Leu-N-(2-phenylethylamide), m.p. 160°–161°
BOC-Phe-Abu-DAMH-Ile-Phe—NH₂, formiate, m.p. 209°–210°
3S-Amino-4S-(BOC-Phe-His-amino)-5-cyclohexyl-pentanoylIle-Phe—NH₂ ("BOC-Phe-His-DACP-Ile-Phe—NH₂"), formiate, m.p. 188° (dec.)
BOC-Phe-His-DAMH-Ile-N-(2,2-diphenylethylamide), m.p. 177°–179°
BOC-Nbg-His-DAMH-Ile-N-(2-phenylethylamide), m.p. 138°–139°
BOC-Tic-His-DAMH-Ile-N-(2-phenylethylamide), m.p. 124°–128°

BOC-(N-Me-Phe)-His-DAMH-Ile-N-(2-phenylethylamide), m.p. 112°–116°
BOC-Ada-His-DAMH-Ile-N-(2-phenylethylamide), m.p. 145° (dec.)
BOC-(D-Phe)-His-DAMH-Ile-N-(2-phenylethylamide), m.p. 163°–165°
BOC-Phe-His-DACP-Ile-N-(2-cyclohexylethylamide), m.p. 155°–156°
BOC-Phe-His-DACP-Ile-DAMH-OMe, m.p. 150°–151°
BOC-Phe-His-DAMH-Ile-(3R,4S)-DAMH-OMe, m.p. 159°–162°
BOC-Phe-His-DACP-Ile-N-(2-phenylethylamide), m.p. 158°–159°
Isovaleryl-Phe-His-DAMH-Ile-N-(2-phenylethylamide), m.p. 174°–175°
Cyclopentylcarbonyl-Phe-His-DAMH-Ile-N-(2-phenylethylamide), m.p. 175°–176°
Acetyl-Phe-His-DAMH-Ile-N-(2-phenylethylamide), m.p. 198°–200°
BOC-Phe-Nle-DACP-Ile-DAMH-OMe, m.p. 191° (dec.)
BOC-Phe-Abu-DAMH-Ile-DAMH-OMe
BOC-Phe-Nle-DAMH-Ile-DAMH-OMe
BOC-Tic-His-DAMH-Ile-DAMH-OMe
BOC-(N-Me-Phe)-His-DAMH-Ile-DAMH-OMe
BOC-Phe-Orn-DAMH-Ile-DAMH-OMe
BOC-Phe-Lys-DAMH-Ile-DAMH-OMe
BOC-Phe-Dab-DAMH-Ile-DAMH-OMe
BOC-(N-Me-His)-His-DAMH-Ile-DAMH-OMe.

EXAMPLE 10

The following compounds are obtained analogously to Example 4 by splitting the corresponding (terminal, obtainable according to Examples 5 or 9) BOC derivatives:

Pro-Phe-His-DAMH-Ile-Phe-OMe, hydrochloride, m.p. 205°–208°
Phe-His-DAMH-Ile-Phe—NH$_2$
Phe-His-DAPP-Ile-Phe-OMe
Phe-His-DAMH-Ile-His-OMe
His-Pro-Phe-His-DAMH-Ile-Phe—NH$_2$, hydrochloride, m.p. 210°
Phe-His-DAMH-Leu-Phe-OMe
Phe-His-DAMH-Ile-N-[2-(4-imidazolyl)-ethyl]-amide
Phe-His-DAMH-Ile-N-(4-piperidyl)-amide
Phe-His-DAMH-Ile-N-(4-pyridylmethyl)-amide
His-Pro-Phe-His-DAMH-Ile-His-OMe
Phe-His-DAMH-Ile-His—NH$_2$
Phe-His-DAMH-Leu-Phe—NH$_2$
His-Pro-Phe-Phe-DAMH-Leu-Phe—NH$_2$
His-Pro-Phe-His-DAMH-Leu-Tyr—NH$_2$.

EXAMPLE 11

Analogously to Example 9, methyl 3S-amino-4S-[3S-amino-4S-(BOC-Phe-His-amino)-6-methylheptanoyl)-Ile-amino]-6-methylheptanoate ("BOC-Phe-His-DAMH-Ile-DAMH-OMe"), m.p. 158°–159° (decomposition), is obtained from methyl 3S-CBZ-amino-4S-[(3S-CBZ-amino-4S-(BOC-Phe-His-amino)-6-methyl-heptanoyl)-Ile-amino]-6-methylheptanoate [m.p. 204°–206°, obtainable from methyl 3S-CBZ-amino-4S-amino-6-methylheptanoate (hydrochloride, m.p. 148°–149°) via methyl 3S-CBZ-amino-4S-(BOC-Ile-amino)-6-methyl-heptanoate, methyl 3S-CBZ-amino-4S-(Ile-amino)-6-methylheptanoate, methyl 3S-CBZ-amino-4S-(3S-CBZ-amino-4S-BOC-amino-6-methyl-heptanoyl-Ile-amino)-6-methylheptanoate and methyl 3S-CBZ-amino-4S-(3S-CBZ-amino-4S-amino-6-methylheptanoyl-Ile-amino)-6-methylheptanoate] by hydrogenolysis.

The following examples relate to pharmaceutical formulations.

EXAMPLE A

Injection Glasses

A solution of 1 kg of His-Pro-Phe-His-DAMH-Ile-Phe—NH$_2$ hydrochloride and 50 g of disodium hydrogen phosphate in 30 l of doubly distilled water is brought to pH 6.5 with 2 N hydrochloric acid, sterile-filtered, filled into injection glasses and lyophilized under sterile conditions and the glasses are closed under sterile conditions. Each injection glass contains 500 mg of active compound.

EXAMPLE B

Suppositories

A mixture of 500 g of BOC-Phe-His-DAMH-Ile-Phe-OMe with 100 g of soya lecithin and 1400 g of cacao butter is melted, poured into molds and allowed to cool. Each suppository contains 500 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

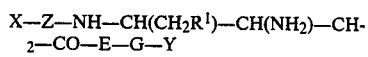

wherein
X is H, $R^2$—O—$C_nH_{2n}$—CO—, $R^2$—$C_nH_{2n}$—O—CO—, $R^2$—$C_nH_{2n}$—CO—, $R^2$—SO$_2$, ($R^2$—$C_nH_{2n}$)—L($R^2$—$C_rH_{2r}$)—$C_tH_{2t}$—CO—, H—(NHCH$_2$CH$_2$)$_n$—NH—CH$_2$CO— or 9-fluorenyl—$C_nH_{2n}$—O—CO—, Z is 3 or 4 amino acid radicals bonded to one another in a peptide-like manner and being Abu, Ada, Ala, Arg, Dab, Gly, His, Ile, Leu, tert.-Leu, Lys, Met, Nbg, Nle, N-Me-His, N-Me-Phe, Orn, Phe, Pro, Ser, Thr, Tic, Trp, Tyr or Val, $R^1$ is H, A, cycloalkyl of 3–7 C atoms, Ar or $C_pH_{2p}$-W, E is absent or is Ala, Gly, Ile, Leu, tert.-Leu, Met, Ser, or Tyr Val, —NH—CH(CH$_2$R$^1$) —CH(NH$_2$) —CH$_2$CO—, Y is —O—$C_mH_{2m}$—R$^3$, —NH—$C_mH_{2m-1}$(R$^3$)$_2$ or NA$_2$, $R^2$ is A, cycloalkyl of 3–7 C atoms, benzyl or Ar, L is CH or N, $R^3$ is H, A, cycloalkyl of 3–7 C atoms, Ar, pyridyl, imidazolyl, piperidyl, N-benzyl-piperidyl or piperazinyl, W is OH, NH$_2$, OA, NHA or NA$_2$, A is alkyl of 1–6 C atoms, Ar is phenyl, phenyl substituted by A, AO, F, Cl, Br, I, CF$_3$ or NH$_2$, or naphthyl, and each of m, n, p, r and t independently is 0, 1, 2, 3, 4 or 5, or a pharmacologically acceptable salt thereof.

2. A compound of claim 1 wherein X is H, POA, BOC or CBA, Z is Pro-Phe-His or His-Pro-Phe-His, $R^1$ is H, ethyl, isopropyl, OH, 2-aminoethyl or 3-aminopropyl, E is absent or is Ile or Leu, G is absent or is His or Phe, Y is OH, OMe or —NH—(CH$_2$)$_2$—$R^3$, $R^3$ is H, phenyl, pyridyl, imidazolyl or N-benzylpiperidyl and m is 0, 1 or 2.

3. A compound of claim 1 wherein X is H, POA or BOC, Z is Pro-Phe-His or His-Pro-Phe-His, $R^1$ is H, isopropyl or phenyl, E is absent or is Ile, G is absent or is His or Phe and Y is OH, OMe, NH$_2$, N-benzyl-4-piperidyl-amino or 2-phenylethylamino.

4. A compound of claim 1 wherein Z is 3 or 4 amino acid radicals bonded to one another in a peptide-like manner which are His, Phe or Pro.

5. A compound of claim 1 wherein Z is Pro-Phe-His or His-Pro-Phe-His.

6. A pharmaceutical composition comprising an amount of a compound of claim 1 effective to inhibit renin and a pharmaceutically acceptable carrier.

7. A composition claim 6 wherein the amount of said compound is 100 mg to 30 g.

8. A method of prophylaxis or treatment of a cardiac, circulatory or vascular disease in a patient comprising administering to the patient a compound of claim 1.

9. A method of prophylaxis or treatment of hypertension, cardiac insufficiency or hyperaldosteronism in a patient comprising administering to a patient a compound of claim 1.

10. A method of inhibiting renin activity in plasma comprising administering a compound of claim 1.

* * * * *